United States Patent [19]
Baratta

[11] Patent Number: 5,528,942
[45] Date of Patent: *Jun. 25, 1996

[54] APPARATUS FOR MAXIMIZING CRITICAL BUCKLING LOADS FOR COMPRESSION TESTING

[76] Inventor: Francis I. Baratta, 138 Ridge St., Arlington, Mass. 02174-1737

[ * ] Notice: The term of this patent shall not extend beyond the expiration date of Pat. No. 5,431,062.

[21] Appl. No.: 490,054

[22] Filed: Jun. 13, 1995

[51] Int. Cl.$^6$ ............................................. G01N 3/02
[52] U.S. Cl. ............................................. 73/856; 73/818
[58] Field of Search ............................ 73/818, 825, 855, 73/856, 857, 858, 859, 860

[56] References Cited

U.S. PATENT DOCUMENTS

| | | | |
|---|---|---|---|
| 3,559,473 | 2/1971 | Dudderar et al. | 73/818 |
| 4,393,716 | 7/1983 | Clark et al. | 73/818 |
| 4,686,860 | 9/1987 | Liu | 73/856 |
| 4,840,070 | 6/1989 | Ralfs et al. | 73/818 |
| 4,850,231 | 7/1991 | Ralfs et al. | 73/859 |
| 5,297,441 | 3/1994 | Smith et al. | 73/818 |
| 5,373,744 | 12/1994 | Parsons et al. | 73/818 |
| 5,388,464 | 2/1995 | Maddison | 73/856 |
| 5,431,062 | 7/1995 | Baratta | 73/856 |
| 5,435,187 | 7/1995 | Ewy et al. | 73/856 |

OTHER PUBLICATIONS

S. Timoshenko, *Strength of Materials*, Part I, 3rd. Ed., D. Van Nostrand Co., N.Y. 1958.

*Primary Examiner*—Richard Chilcot
*Assistant Examiner*—Max Noori

[57] ABSTRACT

Attempts to determine compression properties of materials from specimens having a thin cross-section or even specimens that have relatively large cross-sections and correspondingly large slenderness ratios, i.e., length-to cross-sectional-thicknesses, are thwarted, became failure will occur due to Euler buckling prior to the realization of the objective. The same problem exists when testing columns of various cross-sections and thin-walled cylinders as structural components, depending upon their slenderness ratios, or in situ specimens cut out of thin structural components. This invention presents an improved, but simple way to increase the critical buckling force while mechanically testing in compression laboratory specimens, in situ test specimens taken from structural components, or even structural components having large slenderness ratios. The invention allows the true compression load to be fully developed within the test piece such that the compression properties of the test material can be determined without buckling. This device can be operated at cryogenic, ambient, or elevated temperatures. The invention utilizes a hollow cylinder, termed a bending moment absorber, which is fitted and fixed to the ends of the test specimen. The test specimen can be a dumbbell type, a thin coupon, a thin hollow cylinder, or in situ a specimens cut out of structural components. The test piece can be either pinned or threaded and/or bonded at its ends to the bending moment absorber. The sample can be rectangularly-shaped or have a square-shaped cross-section, wherein semi-circular spacers, with appropriate cut-outs to fit and accommodate the particular cross-sections, which are employed at each end and pinned or threaded and/or bonded between the specimen and the bending moment absorber. These assemblies, in turn are clamped at each end by commercially available hydraulicly-operated grips within the load train. The combined cross-sections of the hollow cylinder and the specimen act in concert so as to markedly increase the moment of inertia of the system and will result in a corresponding increase in the critical buckling load.

24 Claims, 7 Drawing Sheets

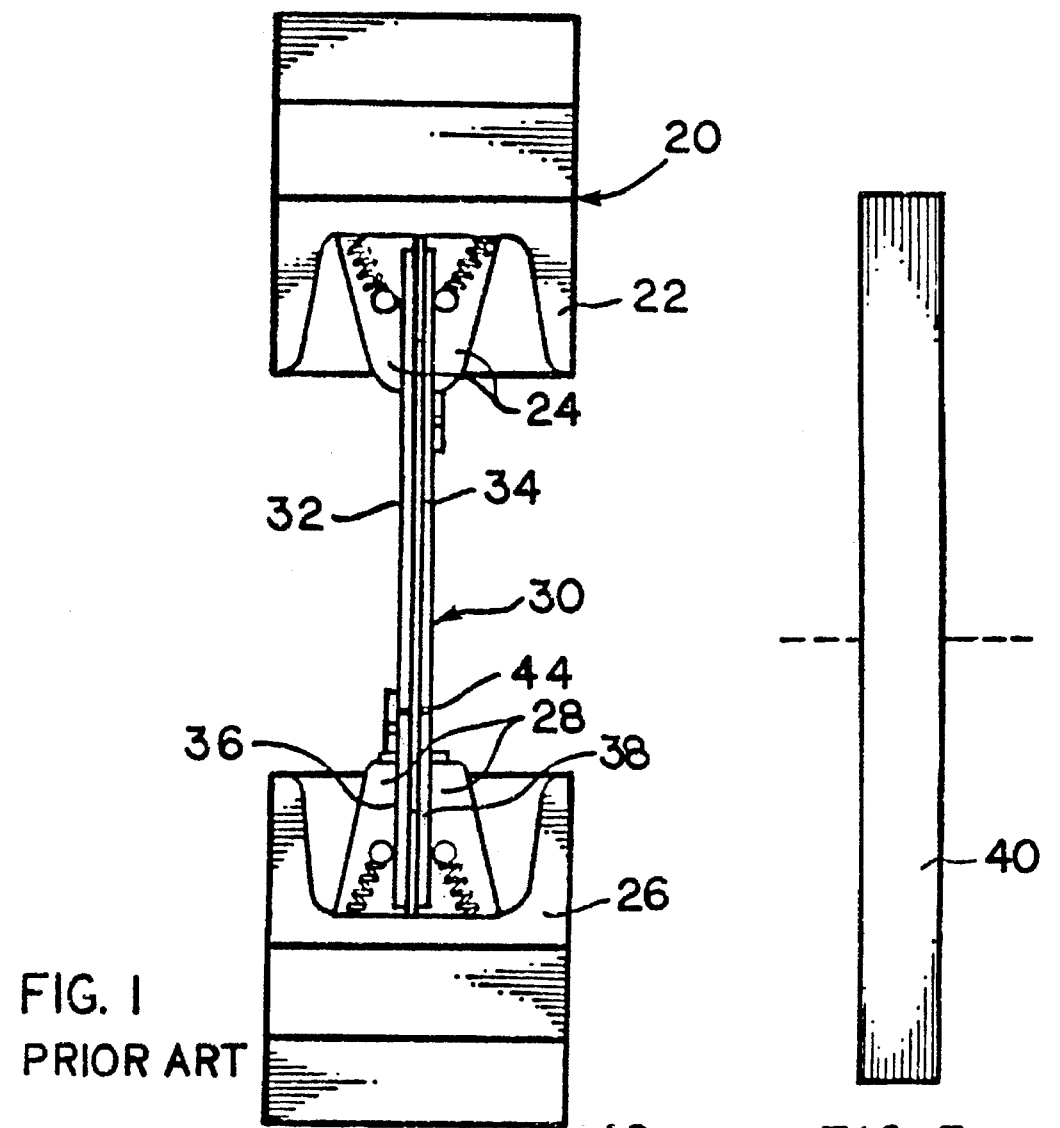
FIG. 1 PRIOR ART
FIG. 3 PRIOR ART
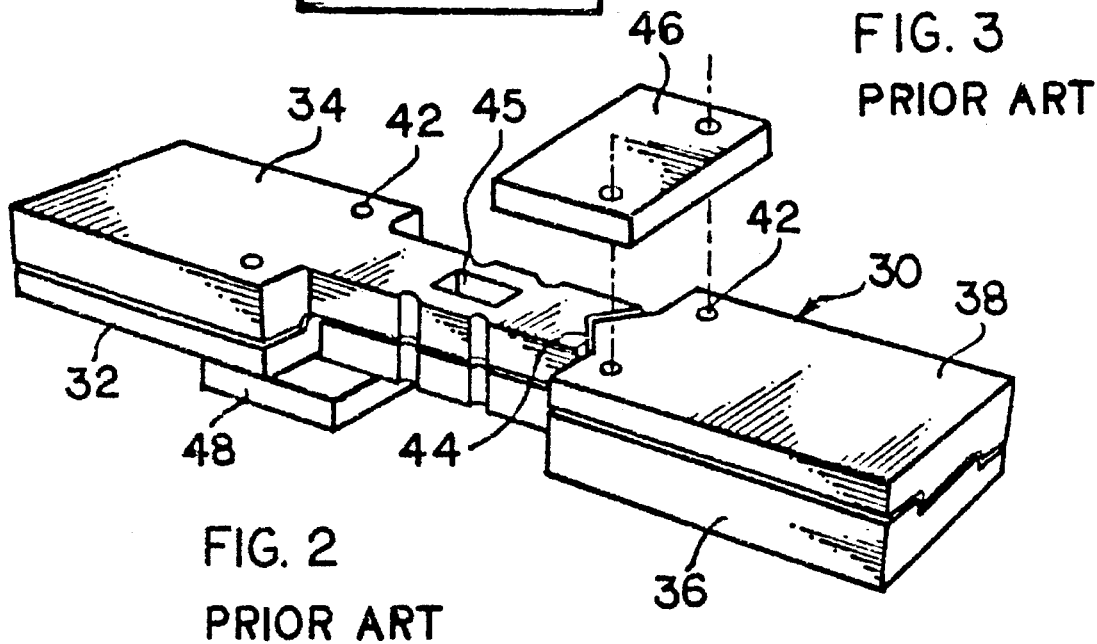
FIG. 2 PRIOR ART

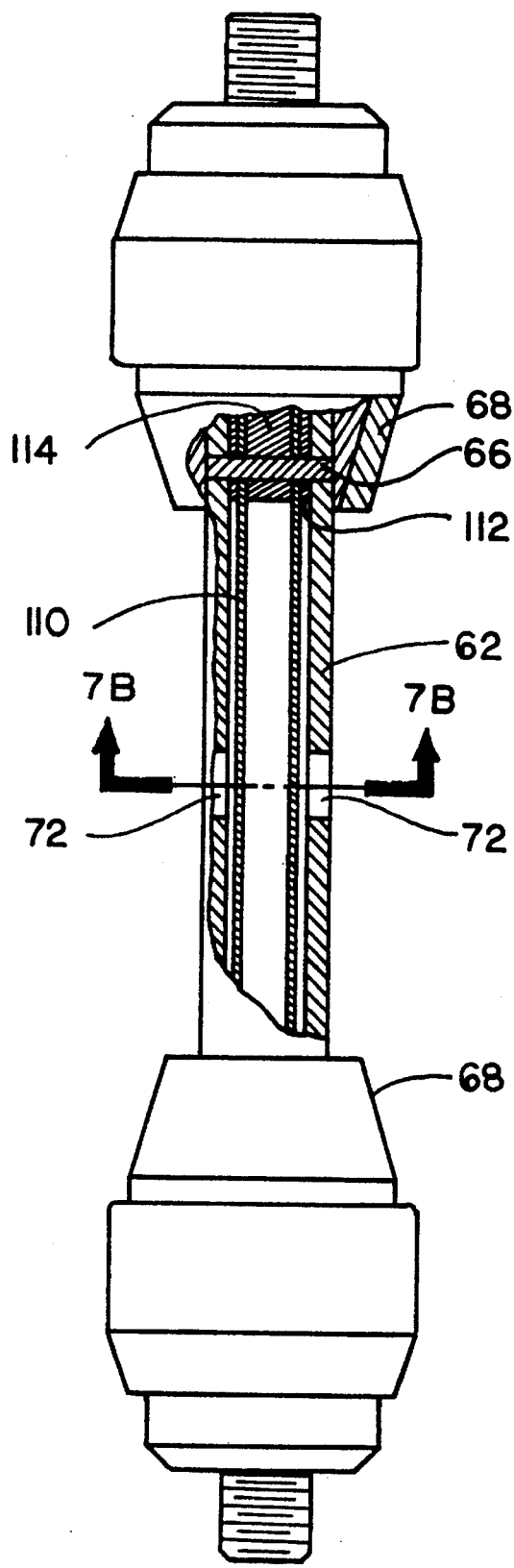
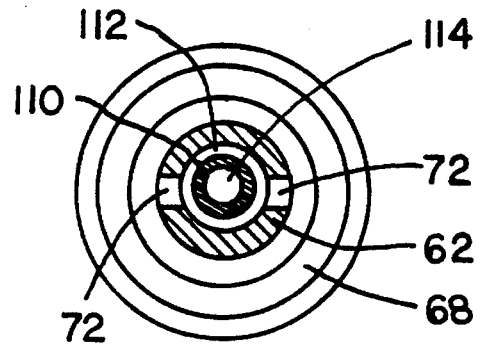
FIG. 7B
FIG. 7A

APPARATUS FOR MAXIMIZING CRITICAL BUCKLING LOADS FOR COMPRESSION TESTING

FIELD OF INVENTION

This invention solves the problem of and need for a simple method of increasing the critical buckling force during compression testing of laboratory specimens, columns of various cross-sections such as circular, rectangular and square etc.; and including thin-walled cylindrical structures, where all of these have large length-thin-cross-sectional-thicknesses called, slenderness ratios, while allowing the applied compressive force to fully develop within the specimen or structure and thus determine valid mechanical compression properties of test materials.

BACKGROUND OF INVENTION AND PRIOR ART

When attempting to determine mechanical properties of homogeneous and composite materials while testing in compression samples taken from components whose slenderness ratio is large, such as thin sheets, columns, or thin-walled tubes, difficulties arise became the Euler column buckling load (see OTHER PUBLICATIONS) will be less than that required to fully test the specimen. Whether the test piece be a metallic, a ceramic, a polymer or a composite material this problem is ever present. Also in the field of mechanics of materials research, thin hollow cylinders are utilized as test specimens to determine the validity of failure hypotheses. Such hypotheses often require multi-axial loading which includes compression stressing. Again, the researcher faces the problem that the thin hollow cylindrical specimen may fail due to Euler buckling, depending upon its slenderness ratio, prior to attaining the desired data.

To demonstrate how Euler column buckling can interfere with the determination of mechanical properties consider the following realistic example: Assume for the sake of demonstration that the exact compression strength or yield stress (or proportional limit) of a thin-walled steel component is desired after fabrication, and it is known that prior to the manufacturing process the compression yield strength is approximately 100 ksi. A test coupon is removed from the structure to determine its compression properties; it has an over all length L of 3 inches and rectangular cross-sectional dimensions of b=½ and t=1/16 inches. Since Py=Sy (A)=Sy (bt)=100 ksi (½ in×1/16 in)=3125 lbs. Py is the expected load when testing in compression to determine the yield strength Sy of the material and A is the cross-sectional area of the test specimen.

The critical Euler buckling load Pcr for a column, or in this case a thin rectangular specimen with clamped end conditions having an axial length of L; and cross-sectional dimensions of length b and thickness t is given by the following general equation:

$$Pcr = 4\pi^2 EI/L^2 \qquad (1)$$

Where E, the modulus of elasticity of the steel material, which is 30 million psi and I is the moment of inertia of the cross-section. In this case:

$$I = bt^3/12 \qquad (1a)$$

Substitution of Eq. 1a into Eq. 1 gives:

$$Pcr = E\pi^2 bt^3/3L^2 \qquad (2)$$

Substitution of the above numerical values into Eq. 1 results in a critical buckling load Pcr of 1339 pounds. It is see from this example that buckling of the specimen will occur prior to obtaining the yield stress Sy of the material and thus the determination of the desired mechanical properties will not be realized.

As seen from the above discussion, when manufacturing various structural components it is desirable to test such structures for mechanical strength. For example, in the airplane industry, some of the airplane parts are made of composite materials. It is desirable to test specimens of these parts for compression strength.

There are machines available to accomplish this type of testing. For example, during compression testing the specimen, such as a flat, thin, homogeneous sample (as already demonstrated) or a composite, sometimes referred to as a "coupon", is supported by a conventional test specimen holder (also referred to as a fixture) between the grips of the testing machine. The machine compresses the coupon along its lengthwise direction until it fails, whereupon the testing machine provides a read-out of the force provided to fail the specimen. Conventional type testing devices provide external support for coupons along their lengthwise axes which is required during compression testing to prevent Euler column buckling. However, test coupons should be supported in a manner so that buckling is eliminated without interfering with the transmission of the full load to each specimen. Also, if the coupon is a composite it should be supported in a manner so that the sublaminate buckling of the specimen, or any natural failure mode of interest is not restricted. In addition, during compression testing it is desirable to attach an extensometer or strain gages to the coupon to measure the amount of deformation or strain during compression.

These conventional fixtures have a large contact area with the test specimen which inherently transfers some of the test load to the fixture itself, resulting in an erroneous overestimate of the coupon's compressive strength. Also, an opening must be cut into the fixture to low for open and filled hole compression tests. This makes it difficult to obtain valid strain measurements in the vicinity of the opening.

Existing compression fixtures support faces of the test specimen. While these fixtures restrict the Euler column buckling, they also restrict the valid sublaminate buckling failure mode of composite samples. Specimen designs based on stable column sections have been used to measure compression properties of composites. However, these specimens have very restrictive application and are not suitable for general use.

A number of conventional support devices has been disclosed in U.S. Patents, see REFERENCES CITED. For example, U.S. Pat. No. 683,184 by Rockwell shows a clamp having four rectangularly arranged blocks connected together in pairs by compression and expansion screws. In addition, U.S. Pat. No. 2,350,060 by Montgomery and U.S. Pat. No. 2,368,900 by Templin disclose compression testing devices for thin specimens that include a pair of T-shaped jaws having small diameter rollers to engage the surfaces of the specimen. And U.S. Pat. No. 4,840,070 by Rolfs et al., utilizes a laminate compression tester which includes a pair of adjustable stabilizing jaws having end segments that engage specimen grips of the testing machine. Finally U.S. Pat. No. 5,297,441 by Smith et al., describes three embodiments: The first embodiment supports the test piece along both of its lengthwise edges while engaging between the grips of the testing machine, in the second the apparatus supports the test piece along only one of its edges, and in the third embodiment, the apparatus includes grip plates which are mounted to the test machine and engage a portion of the test specimen while the remainder of the specimen is supported along its lengthwise edges by stabilizer plates.

All of the above described inventions, to some degree, restrain the applied force such that the force is neither fully allowed to be absorbed by the test piece nor is it accurately known. This results in an erroneous measurement of this force leading to an error in the determination of the compression strength of the test sample.

SUMMARY OF INVENTION

Attempts to determine properties of materials when testing in compression from specimens having a thin cross-section or even specimens that have relatively large cross-sections and correspondingly large slenderness ratios are thwarted, because failure will occur due to Euler buckling prior to the realization of the objective. The same problem exists when testing columns of various cross-sections and thin-walled cylinders as structural components, depending upon their slenderness ratios, or in situ specimens cut out of thin structural components.

This invention presents an improved but simple method of precluding buckling while determining mechanical properties when testing in compression of laboratory test samples, columns and cylindrical structural components. The improvement is due to what has already been previously termed in U.S. patent application Ser. No. 08/242,303 by Baratta, a bending moment absorber. Briefly, the bending moment absorber is described as an assembly that surrounds the specimen with a hollow tube and fixes the ends of the specimen to the tube by mechanical means and forces the two components to behave as one through the use of various connections and/or the use of commercially available hydraulic grips. In this way, the moment of inertia of the combined structure is markedly increased over that of the test piece alone and the effect of the inherent bending moment is greatly reduced. Because one of the major parameters in the Euler column buckling equation, (refer to OTHER PUBLICATIONS; that by Timoshenko) is directly dependent upon the moment of inertia of the cross-section (see Eq. 1 above). Any increase in this cross-sectional property will markedly increase the critical buckling force, and in many testing situations eliminate buckling and allow the full mechanical property description of the test material.

The invention can accommodate a round dumbbell type specimen or one of a different cross-section, i.e., rectangular, square, or it can be a thin hollow cylinder. The test piece can be either pinned or threaded and/or bonded at its ends to the bending moment absorber; or the sample can be rectangularly-shaped or have a square-shaped cross-section, with semi-circular spacers having appropriate cut-outs to fit and accommodate the particular cross-sections, which are employed at each end and pinned or threaded and/or bonded between the specimen and the bending moment absorber, see U.S. patent application Ser. No. 08/242,303 by Baratta. Also, if the modulus of elasticity of the bending moment absorber is less than that of the specimen, while their failure strength ratio is greater than their modulus ratio, then failure will occur in the sample and the bending moment absorber will be reusable.

The device can be readily adapted to commercially available ancillary testing equipment and instrumentation such that it can operate at cryogenic, room, mid-range and at extremes of elevated temperatures and still allow the determination of compressive stress-strain data and failure strength of the test sample.

BRIEF DESCRIPTION OF THE DRAWINGS

FIG. 1 is a side view of a conventional testing machine and a conventional fixture for a test specimen;

FIG. 2 is an isometric view of the conventional specimen fixture shown in FIG. 1;

FIG. 3 is a plan view of a conventional test specimen;

FIG. 7A is a cross-sectional view of a thin hollow cylindrical specimen with filler spacers shown inserted and pinned within the bonding moment absorber and this assembly, in turn, is grasped at both ends by hydraulically-operated collet grips;

FIG. 7B is a cross-sectional view of FIG. 7B, shown for clarity;

PREFERRED EMBODIMENT

Figure 5A:
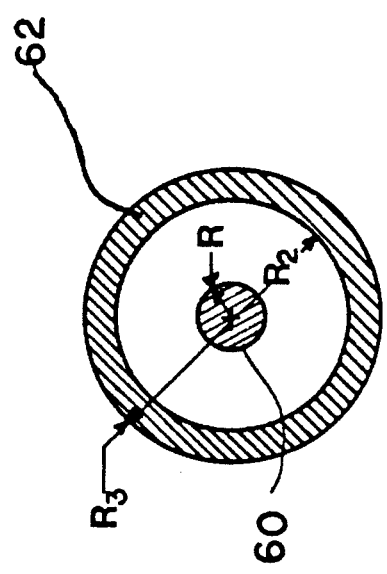
FIG. 5A is a view of a specimen having a circular cross-section and the cross-section of the bending moment absorber.

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

The following paragraphs describe the preferred embodiments, where the figures are discussed in detail to aid in explaining the operating proposed principle. First however, a section entitled Conventional Test Fixtures is presented, followed by a section called Critical Buckling Load. These two sections are presented to better demonstrate the operating principle of the present invention as applied to test specimens which can be considered columns having various cross-sections and then comparing the increase in the critical buckling loads when these configurations are tested in the proposed invention.

Conventional Test Fixtures

As mentioned above, before describing the present invention in greater detail, a brief description of a conventional test fixture and testing machine will be provided which represent those in current use. Referring first to FIG. 1 there is shown a portion of a conventional compression/tension testing machine indicated at 20. In the figure, the the testing machine 20 includes a model 647 hydraulic wedge grip which is part of a MTS 810 test system manufactured by MTS Corporation of Minneapolis, Minn. The testing machine 20 includes an upper wedge 22 having a pair of jaws (also referred to as "grips") 24 and a lower wedge 26 having a pair of grips 28. The grips 24,28 are movable between a closed position (shown in FIG. 1) where the grips engage a conventional specimen fixture indicated at 30 and an open position (not shown) where the grips are spaced apart from the fixture 30.

As shown in FIGS. 1 and 2, the specimen fixture 30 includes an upper large grip portion formed by identical left, right plates 32,34 respectively, and a separate smaller, lower grip portion formed by identical left, right plates 36,38, respectively. A specimen 40 (FIG. 3) having a rectangular plan configuration and a rectangular cross-section is inserted between the left and fight grip plates of the upper and lower grip portions and the opposing plates are then bolted together through openings 42 by bolts (not shown). The grip plates are bolted together to extend entirely across both faces of the specimen 40 and in a manner such that the upper and lower plates are vertically spaced apart from each other slightly by gap 44. A hole 45 is made in one of the plates to allow for open and filled hole compression tests. Briefly, an open hole test involves a rectangular specimen having a circular center hole. The purpose of this test is to determine the influence of properties caused by a hole in the material. On the other hand, a filled hole test uses the same specimen as the open hole test except a fastener is installed in the hole prior to the test. This makes it difficult to obtain measurements of strain, etc. in the vicinity of the hole 45 because if the hole is made large enough to contain the necessary instrumentation to measure strain, there is a high probability of a local buckling failure caused by loss of cross-sectional properties, or specifically the loss of the moment of inertia due to the opening.

With the presence of the gap 44, a slight movement together of the upper and lower portions of the testing machine is permitted in order to determine the compression strength of the specimen 40 and to avoid gross reaction of the compression load through the fixture 30. In order to support the specimen 40 across the gap 44 and to prevent unwanted buckling of the specimen at the gaps, a lower blocking plate 46 is attached to the outer surface of the right grip plate 38 across gap 44, and an upper blocking plate 48 is bolted to the outer surface of the upper left grip plate 32 across another gap 44. Even though the gross reaction of the compressive buckling load is minimized by the gap 44 and blocking plates 46,48 and the sandwiching left and right plates 32,34 (see FIG. 1 and FIG. 2) due to friction there remains a reduction of the load transfer from the testing machine to the sandwiched specimen 40 causing inaccurate mechanical property determination.

The principle that allows the increase in the critical buckling load in the mechanical property determination when testing in compression using the present invention is mathematically demonstrated in the following:

Critical Buckling Load

Figure 4A:
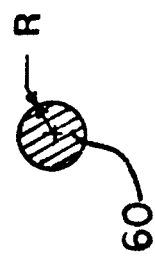
FIG. 4A is a view of a circular cross-sectioned specimen.
Figure 4B:
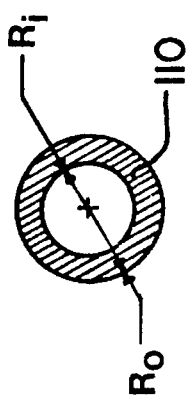
FIG. 4B is a view of a thin hollow cylindrical cross-sectioned specimen.
Figure 4C:
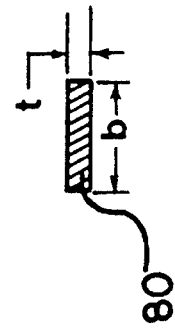
FIG. 4C is a view of a thin rectangular cross-sectioned specimen.

In order to show the operating principle of the proposed invention, the buckling loads for different columns having three cross-sectional shapes are determined: a solid circular cross-section 60, a thin hollow cylinder 110 and a rectangular cross-section 80; each of these shapes are shown in FIGS. 4A, 4b, and 4C, respectively. These columns, or specimens, are then presumed to be tested in the proposed device, such as that shown in FIGS. 6A and 6B; 7A and 7B; and 8A and 8B where the addition of the bending moment absorber 62, shown in the cross-sections given in FIGS. 4A, 4B, and 4C, demonstrates the improvement for each case.

The critical buckling load for a column with fixed ends is given by Eq. 1 above. Note that one of the important parameters is the moment of inertia of tho cross-section. The moment of inertia of the cross-sections shown in FIGS. 4A, 4B, and 4C, which will be called Case 1, Case 2 and Case 3, respectively are:

$$I_1 = \pi R^4/4, \tag{3}$$

$$I_2 = \pi[R^4o - R^4i]/4, \text{ and} \tag{4}$$

$$I_3 = bt/12 \tag{5}$$

Where R is the radius of the circular cross-section (FIG. 4A), Ro is the outer radius and Ri is tho inner radius of the thin hollow cylinder (FIG. 4B) and b and t are the length and thickness of the rectangular cross-section (FIG. 4C).

Figure 5B:
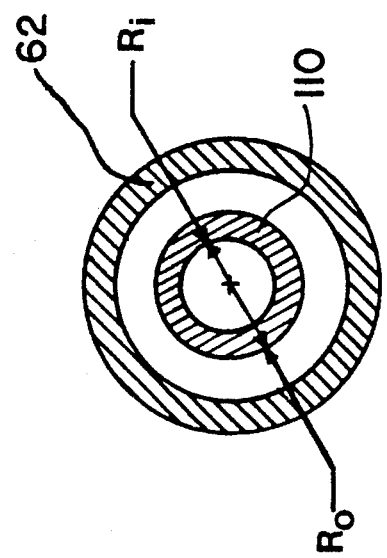
FIG. 5B is a cross-sectional view of a thin hollow specimen and the cross-section of the bending moment absorber.
Figure 5C:
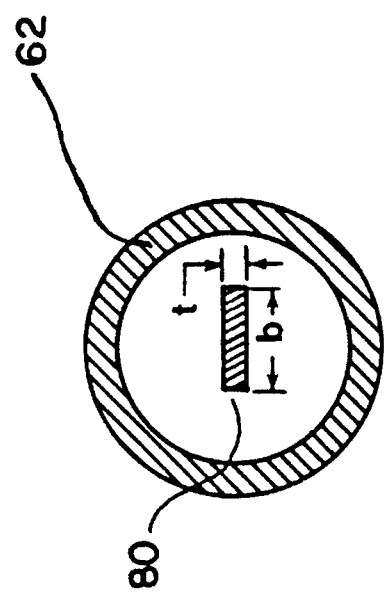
FIG. 5C is a view of a specimen having a thin, rectangular cross-section and the cross-section of the bending moment absorber.

Consider now encompassing tho each of these specimens with a hollow cylinder, called the bending moment absorber, and being of the same material as the specimens. The ends of each specimen are fixed to the bending moment absorber 62 and each end clamped by commercially available hydraulically-operated grips 68, as shown for example in FIGS. 6A and 6B; 7A and 7B; and 8A and 8B. Now the moment of inertia of each of these combined cross-sections, shown in FIGS. 5A, 5B, and 5C, associated with Cases 1, 2, and 3, respectively are:

$$I_1 = \pi[R^4 + (R^4_3 - R^4_2)]/4, \tag{6}$$

$$I_2 = \pi[(R^4o - R^4i) + (R^4_3 - R^4_2)]/4, \text{ and} \tag{7}$$

$$I_3 = b^3t/12 + \pi(R^4_3 - R^4_2)/4 \tag{8}$$

Where $R_3$ and $R_2$ are the inner and outer radius of the bonding moment absorber, respectively, as shown in FIG. 5A; and indicated in FIGS. 5B, and 5C.

Because the remaining parameters in Eq. 1, i.e., $\pi$, E, and L, the general formula for the critical buckling load, are the same for both the single cross-sections and the combined cross-sections, a comparison of buckling loads can be effected by simply dividing each of the above equations by the equation representing the respective moment of inertia of the single cross-section, e.g., divide Eq. 6 by Eq. 3, etc. These operations result in the following equations that define the critical buckling ratios $R_{cr1}$, $R_{cr2}$, and $R_{cr3}$:

$$R_{cr1}=1+(R_3/R^4)-(R_2/R^4), \qquad (9)$$

$$R_{cr2}=1+(R^4{}_3-R^4{}_2)/(R^4o-R^4i) \qquad (10)$$

$$R_{cr3}=1+3\pi(R^4{}_3-R^4{}_2)/bt^3 \qquad (11)$$

The above formulas mathematically indicate the idealized improvement in the critical buckling load when utilizing the proposed invention; for example consider each of the three cases by assigning practical numbers to the various parameters. Therefore, let: R=¼ in., Ri=0.40 in., Ro=0.50 in., b=½ in, t=1/16 in, $R_3$=0.70, $R_2$=0.60 in.

Calculations for the critical buckling ratio according to Eqs. 9, 10, and 11 are summarized in the following table:

| case: | Critical Buckling Ratio |
|---|---|
| 1 | 29.3 |
| 2 | 3.4 |
| 3 | 8,532 |

The above table demonstrates the gain in the critical buckling force by using the presented invention as a function of the type of test specimen shown in FIGS. 4A, 4B, and 4C. It is noted that the critical buckling load was 1339 pounds as obtained for the rectangularly cross-sectioned specimen from Eq. 1, for the example previously cited, case 3. But, if the present device had been employed the increase in force to cause buckling as indicated in the above table, would have been 8,532 times greater than 1339 pounds. This is an idealized result became the fixity at the ends of the specimen will not be completely rigid. Nevertheless, the gain in the critical buckling load will be considerably greater than 1339 pounds and certainly greater than than the yield load of 3125 pounds, and thus the determination of the desired mechanical property evaluation could have been readily realized.

Figures 9A, 9B:
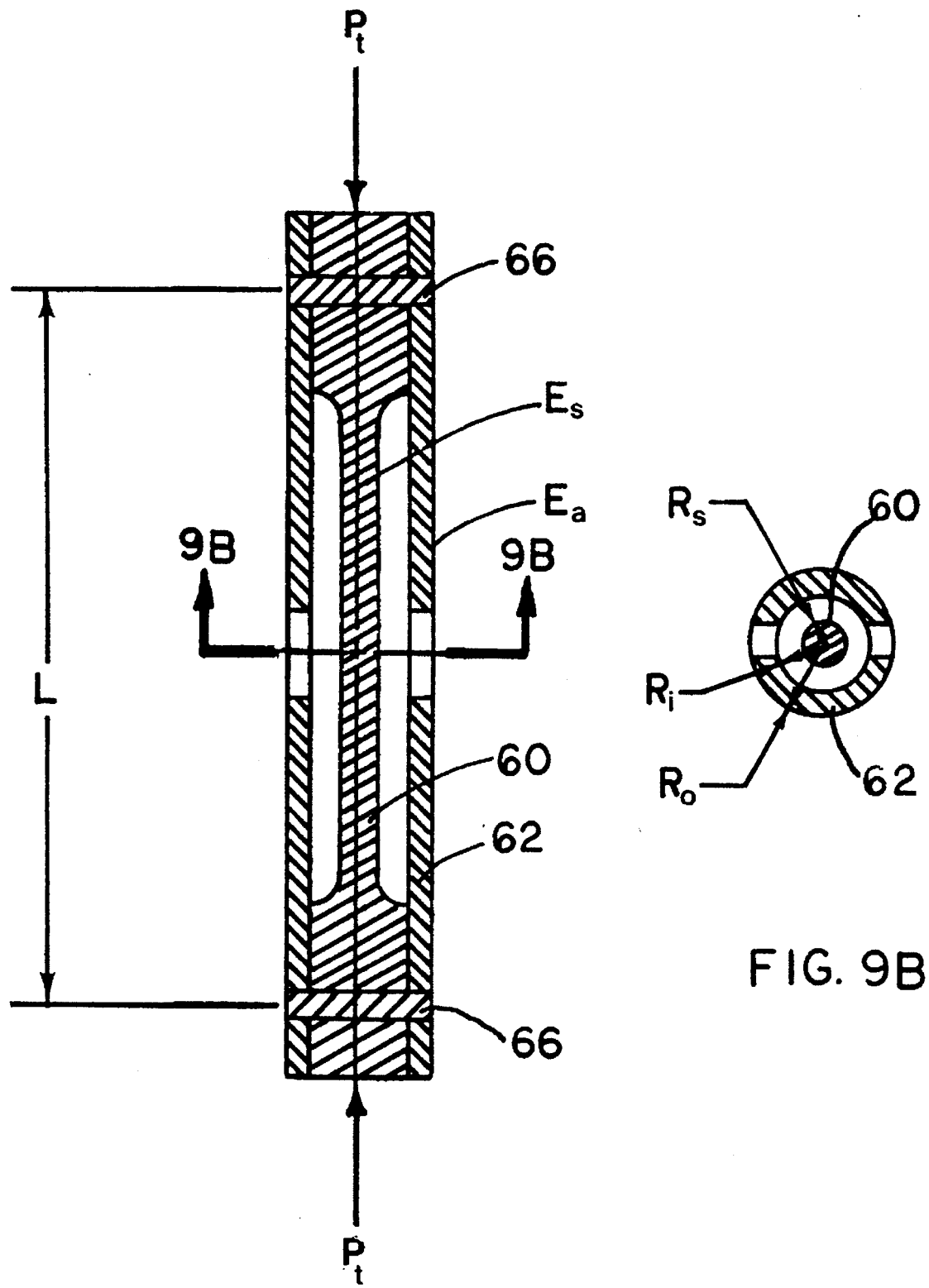
FIG. 9A is a cross-sectional view of of a round dumbbell specimen inserted and pinned within the bending moment absorber.
FIG. 9B is a cross-sectional view of FIG. 9A, shown for clarity.

So as to be able to obtain the compression properties of the specimen material, the load distribution from the testing machine to the bending moment absorber and the specimen needs to be known; consider the following analysis:

Referring to FIG. 9A and FIG. 9B, it is assumed that the bending moment absorber and the specimen are of different materials each having a modulus of elasticity of Ea and Es, respectively. Also the connections, such as the pins 66, at the bending moment absorber interfaces with the specimen are considered to be rigid, i.e., the assembly acts as one solid body. This is not completely correct in that there will be some flexibility at the interfaces, but this can only be determined by experimentation. Nevertheless, it shall be assumed that the ideal case exists so as to simplify the mathematics and easily demonstrate the operating principle.

In FIG. 9A, the axial displacement ds of the specimen 60 and the displacement da of the bending moment absorber 62 during testing (where both having a fixed length of L) are: ds=L Es and da=L Es, respectively, but ds=da, and L(Ss/Es)=L(Sa/Ea). Where Ss and Sa are the axial stresses in the specimen and the absorber, respectively; also Es and Ea are the axial strains in the specimen and the bending moment absorber, respectively. Note that for simplicity the diameter of the heads of the specimen are assumed to be the same diameter as its gage section. Therefore:

$$Ss/Es=Sa/Ea, \text{ or } Sa=Ss(Ea/Es) \qquad (12)$$

Also the total load Pt to the specimen and the bonding moment absorber is:

$$Pt=Ss\,As+Sa\,Aa \qquad (13)$$

And utilizing Eq. 13, we obtain:

$$Pt=Ss[As+Aa(Ea/Es)] \qquad (14)$$

Equations 13 and 14 will allow an estimate of the idealized load distribution between the bending moment absorber and the specimen. However, a more exact method using experimental techniques is subsequently suggested so as to accurately determine the mechanical properties of the specimen material.

Figures 6A, 6B:
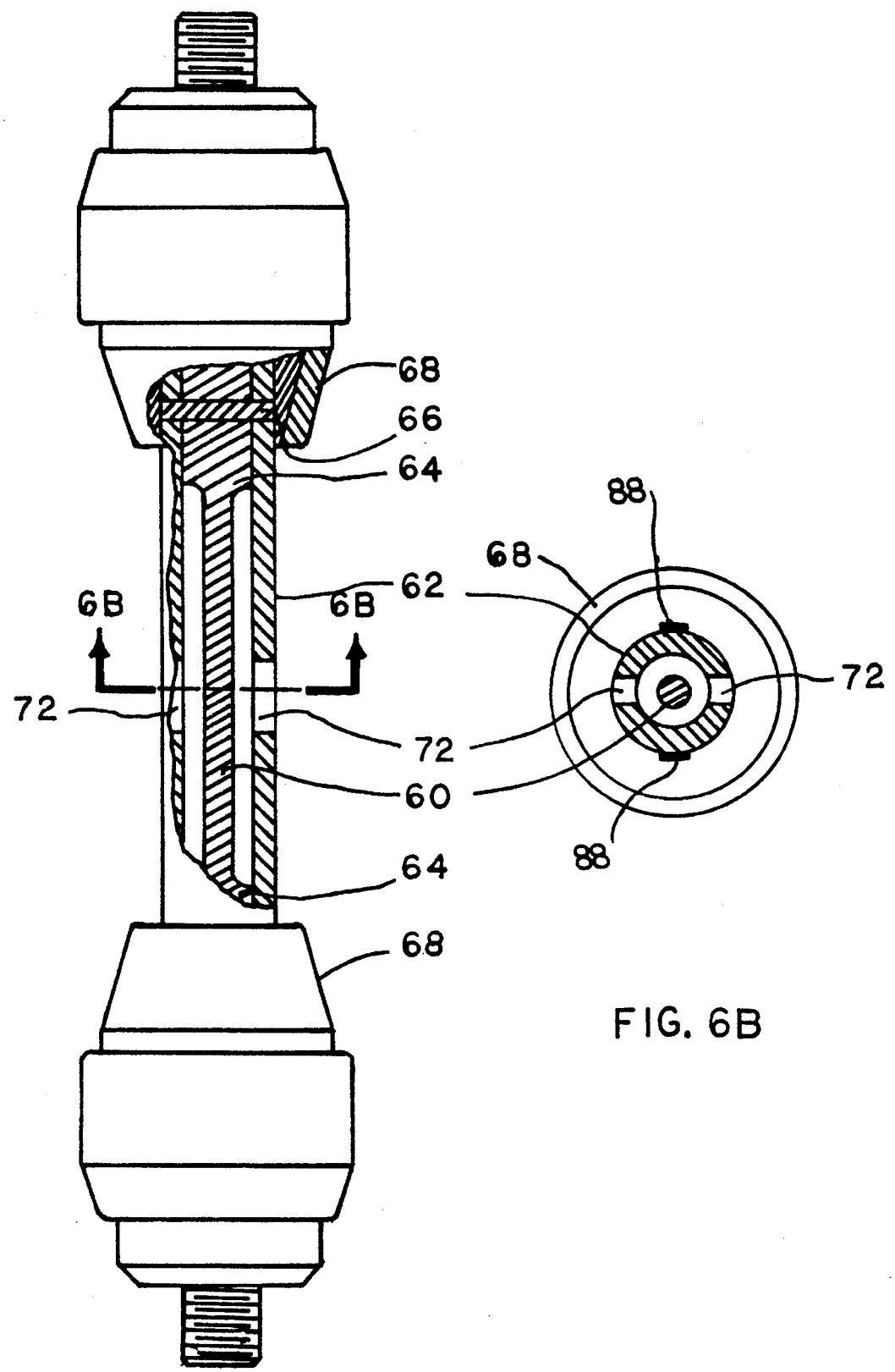
FIG. 6A is a cross-sectional view of a round dumbbell specimen shown inserted and pinned within the bonding moment absorber and this assembly, in turn, is grasped at both ends by hydraulically-operated collet grips.
FIG. 6B is a cross-sectional view of FIG. 6A, shown for clarity.

Now turning to the present invention, which pertains to an apparatus for compression testing an elongate workpiece, a specimen in the form of a dumbbell shape, shown in FIGS. 6A and 6B. The apparatus includes a hollow cylinder, termed a bending moment absorber 62, which encompasses the workpiece, or test specimen 60. The bending moment absorber is closely fitted and pinned 66 or can be threaded and/or bonded to the ends of dumbbell specimen. Rectangularly-shaped or square-shaped cross-sectioned specimens can also be tested by utilizing appropriate spacers at its ends which are then pinned or threaded and/or bonded to the bending moment absorber; this will be discussed later. These assemblies, in turn, are clamped at their ends by commercially available hydraulically-operated grips 68, shown in FIG. 6A as 6B, within the load train, thus forcing the specimen to act as an integral part of the bending moment absorber 62. The moment of inertia of the combined cross-sections of the assembly, including the specimen is markedly increased. The bending moment absorber has a very large cross-sectional moment of inertia compared to that of the specimen (if it were to act alone). This markedly increases the moment of inertia of the assembly and thereby increases the critical force at which buckling will occur; at the same time, the axial compression force is allowed to be distributed from the testing machine to the specimen without restraint.

When testing in the linear mode regime, i.e., linear response of the material, the material for the bending moment absorber can be chosen to be dissimilar to that of the specimen such that the modulus of the elasticity ratio of the bending moment absorber to that of the specimen is less than 1.0; while their yield strength ratio is greater than their modulus ratio. Because the bending moment absorber and the specimen are fixed to each other, the load distribution during testing can be determined. With the aid of appropriate instrumentation and prior knowledge of the modulus ratio, the stress applied to the specimen will be known, as well as stress-strain dam during testing. Failure will occur in the test specimen before the bending moment absorber reaches its yield or failure stress and thus be reusable.

A similar approach can be adopted for testing in a nonlinear mode, i.e., testing in the extremes of elevated temperatures, by heating only the specimen and cooling the encompassing bending moment absorber. Again, if the bending moment absorber and specimen are initially of dissimilar materials and their modulus of elasticity ratio is less than 1.0; with the use of appropriate instrumentation the stress-strain curve of the specimen material will be known, as well as its compressive properties. As before, the bending moment absorber will be available for reuse.

Alternatively, the bending moment absorber can be fabricated from the same material as the specimen and this assembly heated for testing in the nonlinear mode of operation. With appropriate instrumentation the desired compressive properties of the test material will be known.

It is noted that most engineering materials when heated, and when being tested within the elastic regime will, nevertheless, exhibit a lesser modulus of elasticity than that obtained at ambient conditions, and therefore will be less stiff so that specimens of large slenderness ratios will have greater tendency to buckle. The use of the proposed invention in such a condition allows the bending moment absorber to provide an increase in the moment of inertia and thus will reduce the possibility of critical buckling.

Again referring to FIG. 6A and FIG. 6B, the axial strain can be monitored via electric-resistance strain gages 88 bonded to rite bending moment absorber 62, or for elevated temperature operation, the axial displacement of the bending moment absorber can be obtained using laser type extensometers (not shown). An additional extensometer can simultaneously be aimed through the ports 72 at the specimen gage diameter during elevated temperature operation. This allows the knowledge of the displacement or strain in the specimen 60 due to compressive loading and various temperature environments, and thus the stress as a function of temperature and the strength of the material can be determined. Further mathematical details of testing in the linear and nonlinear tensile mode of operation are given in U.S. patent application Ser. No. 08/242,303; they are applicable to the compressive mode of testing as well, and thus are not repeated here.

To insure intimate contact during cryogenic temperature testing, the bending moment absorber material can be chosen such that its linear coefficient of thermal expansion is greater than that of the specimen material. At elevated temperatures the chosen thermal expansion ratio should be reversed. Ambient temperature testing will require a slip-fit between the bending moment absorber and the specimen. The specimen material, the temperature at which testing is to be accomplished, and the ratio of the modulus of elasticity of the bending moment absorber to the specimen material will dictate the material to be used for the bending moment absorber. Further discussion of such details are not necessary to the understanding of the presented concept.

Figures 8A, 8B:
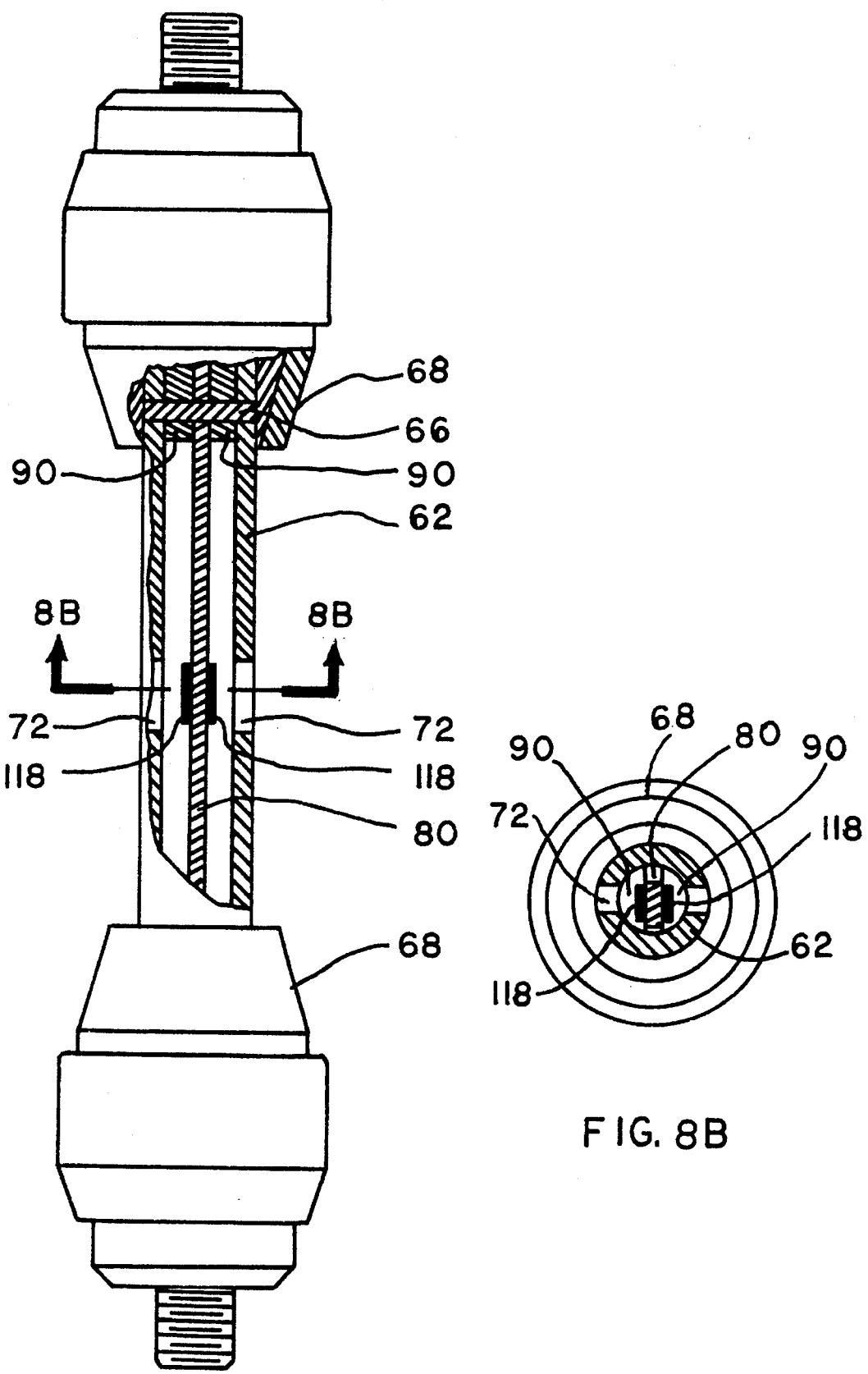
FIG. 8A is a cross-sectional view of a thin, rectangular specimen (a coupon) shown inserted and pinned with spacers within the bending moment absorber and this assembly, in turn, is gasped at both ends by hydraulically-operated collet grips.
FIG. 8B is a cross-sectional view of FIG. 8A, shown for clarity.

The test fixtures shown in FIGS. 6A, 7A and 8A can be used for both static and dynamic loading at various temperature environments. However, even though dynamic loading with its required ancillary equipment and instrumentation can be an adjunct to the static fixtures, is not further discussed because it is not necessary to the understanding of the principle of the invention. Therefore, only static loading at various temperature environments have been considered and discussed. Nevertheless, such discussions are germane to the dynamic loading regime, as well.

Turning now to the first embodiment and returning to FIGS. 6A, and 6B, a dumbbell specimen 60 is shown inserted and pinned 66 at each of its head-ends 64 within a tube, called a bending moment absorber, 62; this tubular sleeve also has ports 72 that low deflection observations of the specimen and strain gages 88 that allow strain determination. The bending moment absorber and the specimen are fitted snugly or even slightly shrink-fitted within each other to insure intimate contact at their interfaces. The assembly in turn is grasped by commercially available hydraulic grips 68. The dumbbell specimen 60, with accompanying holes for pins 66, or threaded holes for bolts or screws, can be designed within the present state-of-the art and the pin, bolt or screw material chosen, such that failure will be insured within the central gage section of the specimen design. It is noted that only the pins are shown for demonstrative purposes.

In the above described embodiment the bending moment absorber 62 is a tube which has drilled holes at the top and bottom and a prepared sample or specimen 60 with matching top and bottom holes is encompassed by the bending moment absorber. Each hole in the bending moment absorber is connected by a pin, bolt or screw (these not shown) to a matching hole in the sample. These fasteners may terminate within the sample or may be drilled through the sample and engage holes on both sides of the tube. At least one through-pin, bolt or screw or two terminating pins, bolts or screws aligned oppositely on the sample will be used at each end of the sample.

There are a number of various fastening methods other than that given above that are further described below, but for the sake of clarity are not presented in the figures:

The important first embodiment shown in FIG. 6A is the bending moment absorber 62 connected to the specimen 60 and the assembly rigidly clamped together by the hydraulically-operated grips 68 while being loaded in compression. As previously mentioned, the bending moment absorber acts to increase the moment of inertia from only that of the specimen, if it were being tested alone, to that of the complete assembly, thus markedly increasing the critical buckling load.

Returning to FIG. 6A and FIG. 6B, ports 72 are provided in the bending moment absorber 62 to allow observation of the specimen 60 during testing for extensometer measurements or to provide openings for the lead wires attached to the strain gages (not shown). Strain gages 88, as shown in FIG. 6B, can also be bonded to the outside of the bending moment absorber. In this way the distribution of the known load from the mechanical testing machine to both the specimen 60 and the bending moment absorber 62 will also be known, if the modulus of elasticity of each material has been determined previously. Alternatively, if only one of the members is strain-gaged the force transmitted to the other member can be deduced since the total force is known from the testing machine. In addition, the stress-strain curve of the test specimen material within the elastic region can also be obtained which will allow the determination of the compressive strength of the material.

FIGS. 7A and 7B show a thin hollow specimen 110 with closely fitted cylindrical filler spacers 112 and 114 located at each end of the sample (but shown only at one end for convenience). These components are encompassed by the closely fitted bending moment absorber 62 with ports 72, which in turn are pinned 66 together. The assembly is gripped at its ends by commercially available hydraulically-operated grips 68. Although the strain gages are not shown so as to simplify the drawings, they can be bonded to the specimen/and or the bending moment absorber for displacement determination. The bending moment absorber, the spacers and the pins can be fitted snugly to each other or even slightly shrink-fitted within each other to insure intimate contact at their interfaces. It is noted that only the pins are shown for demonstrative purposes and for the sake of clarity only these connectors are shown in the figures. However, there are many fastener methods that can be employed and these are subsequently discussed.

A rectangular cross-sectioned coupon, shown in FIGS. 8A and 8B, or a square cross-sectioned specimen (not shown), that can be stressed in a compressive mode, can also be tested in an arrangement similar to that shown in FIG. 6A and FIG. 6B. FIGS. 8A and 8B show the complete assembly, where the coupon 80, is sandwiched at its ends by semi-cylindrical spacers 90 and pinned 66 or joined in the same ways described above at both ends (only one end is shown cross-sectioned) to the encompassing bending moment absorber 62; this in turn is gasped at its ends by a set of hydraulically-operated grips 68. Again, swain gages on the bending moment absorber (not shown), or an extensometer can be used to obtain the strain in the bending moment absorber 62. The displacement of the coupon (or square cross-sectioned specimen) can be obtained by strain gages 118, or observed with an extensometer through the ports 72 of the bending moment absorber provided for that purpose.

A second embodiment where the prepared sample is slip-fitted into the bending moment absorber and these two components are damped together at the top and bottom ends by mechanically activated devices, such as two drillpress chucks, or two mechanically operated collet grips; this assembly in turn is further clamped together by two hydraulically-operated grips attached to the ends of the testing machine. Alternatively, a set of hydraulically-operated grips can be used in place of the mechanically operated devices. Also, shrink-fitted or threaded joints, or encapsulation of the specimen ends within the inside diameter of the bending moment absorber with a low temperature melting, metallic material, and/or bonding, such as adhesive bonding, brazing or welding, can replace the pinned joints at the specimen head-ends, or a combination thereof can be employed.

In a third embodiment the bending moment absorber can be fabricated from any appropriate structural material including a polymer, cast as a hollow cylinder around the specimen or where the prepared sample is placed within a mold and a material with a very low modulus of elasticity compared to that of the specimen, such as a catalyzed elastomer for example, molded as a tube around the sample, providing grip surfaces at the top and bottom that are molded to the sample. (Note that if the modulus of elasticity of the bending moment absorber is very much less than that of the the specimen, then the axial stress in the absorber approaches zero; see Eq. 12 above). Knurled or serrated surfaces in the grip area may be used to enhance the adhesion between the elastomeric material and the sample, as long as the surface modifications have no effect on the sample or the subsequent test results.

In a fourth embodiment the surrounding tube, the bending moment absorber, be a metallic, ceramic, a polymeric, or a composite tubular sleeve which has an interference fit with the prepared sample. The tube is heated to an elevated temperature in an oven or any other appropriate device, such as a hot plate, then slipped over the prepared specimen which is chilled. The tube is cooled causing a tight interference fit at the ends of the prepared sample, which can be fitted into a testing machine.

In a fifth embodiment, a high temperature steel such as a superalloy steel, or a ceramic material can be utilized as a bending moment absorber, with an interference fit joining the top of the prepared sample to the top end of the bending moment absorber and the bottom end of the prepared sample to the bottom end of the bending moment absorber, allowing its use at high testing temperatures.

In a sixth embodiment the bending moment absorber material can be chosen to have an appropriate linear coefficient of thermal expansion compared to the test sample such that the bending moment absorber radially compresses the sample at its top and bottom ends when testing at both cryogenic and elevated temperatures.

In a seventh embodiment the bending moment absorber material can be chosen such that its modulus of elasticity is less than that of the prepared sample specimen. In this way the specimen during testing supports a major portion of the applied force and will fail leaving the bending moment absorber intact for reuse.

An eighth embodiment allows the bending moment absorber system to be used not only for applying either static or dynamic forces in compression, but to apply torque, tension or a combination of these forces, as well as fatigue, if desired.

Figure 10A:
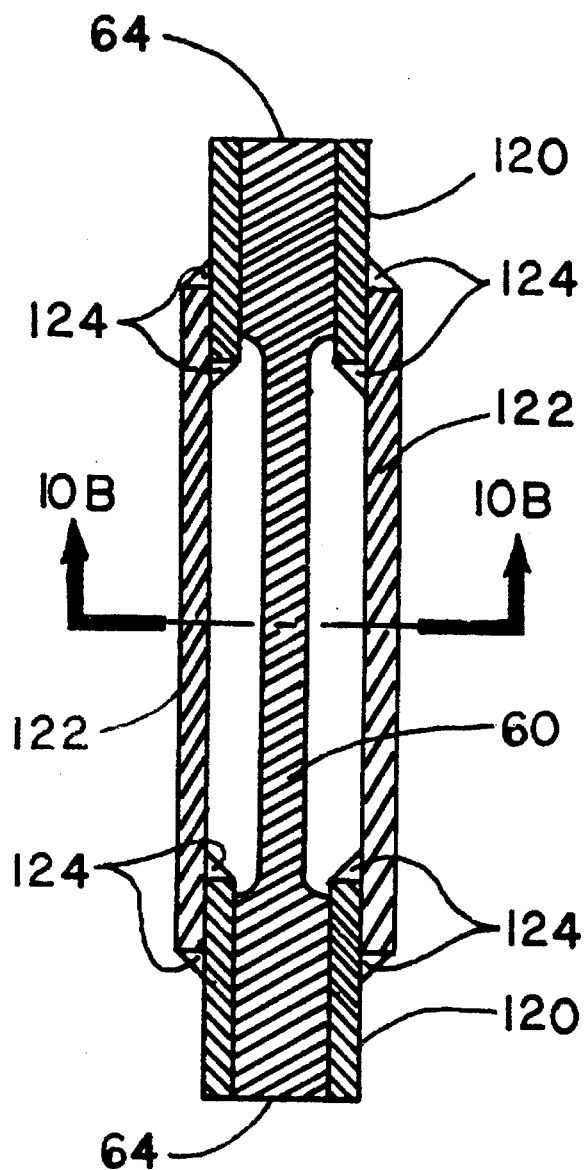
FIG. 10A is a cross-sectional view of a dumbbell specimen shown inserted and shrunk-fitted within a bending moment absorber in the form of a strut assembly.
Figure 10B:
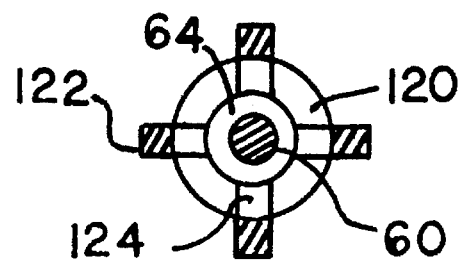
FIG. 10B is a cross-sectional view of FIG. 10A, shown for clarity.

A ninth embodiment is shown in FIG. 10A and FIG. 10B, where a plurality of strut elements 122 joined by any of the present state-of-the-art joining methods that will bond in a rigid manner, such as welding 124 to hoops 120 fitted and fixed, by means previously described, to the head ends 64 of the specimen can also be employed. The marked increase in the moment of inertia provided by the bending moment absorber in the form of strut assembly, 120 and 122 acting in concert with the specimen 60 provides a respondingly large increase in the critical buckling force during compression testing.

I claim:

1. A method to determine the compression properties of a material where a sample of said material is prepared for testing, said sample having a top end and a bottom end, said top and said bottom ends providing grip surfaces for a testing machine and said sample is firstly enclosed within surrounding means which has an upper end and a lower end; said surrounding means are secondarily closely fitted to said sample top end and said sample bottom end, and where, thirdly, the sample is clamped where said top end of said sample is affixed by affixing means to the upper end of said surrounding means, and where said bottom end of said sample is affixed by affixing means to said lower end of said surrounding means, and where said sample and surrounding means are finally clamped by clamping means within a testing device and when, the test device is then activated, the surrounding means, acts as a bending moment absorber, which increases the moment of inertia of said sample precluding the possibility of critical buckling.

2. The claim in 1 where said sample is a test specimen having a dumbbell shaped cross-section, or a thin hollow cylindrical cross-section, or is a thin rectangularly-shaped cross-sectioned coupon removed from a structural component.

3. The claim in 2 where said surrounding means is a tube.

4. The claim in 2 where said surrounding means is a plurality of strut members affixed to hollow cylinder ends.

5. The claim in 2 where said affixing means is a pin or bolt.

6. The claim in 2 where said affixing means is an adhesive joint.

7. The claim in 2 where said affixing means is a shrink fit between the surrounding means and the top end of the sample and the surrounding means and the bottom end of the sample.

8. The claim in 2 where said affixing means is a threaded joint.

9. The claim in 2 where said affixing means is a soldered joint.

10. The claim in 2 where said affixing means is a brazed joint.

11. The claim in 2 where said affixing means is encapsulation within a cast or poured elastomer.

12. The claim in 2 where said affixing means is encapsulation of the specimen ends within the surrounding means with a metallic material having a low melting temperature.

13. The claim in 2 where said clamping means are mechanically activated joints, such as two drillpress chuck mechanisms or two collet grips or two hydraulically-operated grips located at each end of the surrounding means, which is a bending moment absorber.

14. The claim in 2 where said clamping means are two hydraulically-operated jaws located at each end of the surrounding means, called a bending moment absorber.

15. The claim in 2 where said surrounding bending moment absorber tube is a super alloy steel or a ceramic tube, thus allowing a functional bending moment absorbing method for high temperature tests of metals and ceramics.

16. The claim in 2 where said surrounding bending moment absorber tube material is chosen to have a linear coefficient of thermal expansion less than that of the prepared sample, such that a radial compression is provided at the top and bottom ends of the test sample when testing at elevated temperatures.

17. The claim in 2 where said surrounding bending moment absorber tube material is chosen to have a linear coefficient of thermal expansion greater than that of the prepared sample, such that a radial compression is provided at the top and bottom ends of the test sample when testing at cryogenic temperatures.

18. The claim in 2 where said surrounding bending moment absorber material is chosen to have a lower modulus of elasticity than that of the prepared sample, such that the sample will support a greater portion of the applied load and thus fail; leaving the bending moment absorber intact and allowing it to be reusable.

19. The claim in 2 where said surrounding bending moment absorber is used for static testing.

20. The claim in 2 where said surrounding bending moment absorber is used for dynamic testing.

21. The claim in 2 where said surrounding bending moment absorber is used for cyclic fatigue testing.

22. The claim in 2 where said surrounding bending moment absorber is used to apply a multiplicity of loadings, such as tension, compression, torque and a combination thereof.

23. A device to test specimens that are columnar in form where a prepared sample, which has a top end and a bottom end enclosed within a surrounding sleeve which is a bending moment absorber which has a top end and bottom end, where said prepared sample is affixed at said top end to said top end of said surrounding sleeve and where said prepared sample is affixed at its said bottom end to said bottom end of said surrounding sleeve and where said top end of said surrounding sleeve is gripped by the top jaw of a testing machine and where said bottom end of said surrounding sleeve is gripped by the bottom end of the bottom jaw of a testing machine, and where said surrounding sleeve, which is a bending moment absorber, acts to align said top and bottom ends of said sample within said testing machine; preventing premature failure by buckling of said test sample.

24. A method to test specimens that are columnar in form where a prepared test sample is enclosed within a closely conforming tubular sleeve or bending moment absorber to contain it, and affixed to said tubular sleeve at each end, and where the ends of said tubular sleeve and said contained sample are gripped within a testing machine, where said tubular sleeve provides additional moment of inertia to the said prepared test sample it contains and reduces possibility of buckling.

* * * * *

UNITED STATES PATENT AND TRADEMARK OFFICE
CERTIFICATE OF CORRECTION

PATENT NO. : 5,528,942
DATED : Jun. 25, 1996
INVENTOR(S) : Francis I. Baratta

Page 1 of 9

It is certified that error appears in the above-identified patent and that said Letters Patent is hereby corrected as shown below:

The title page should be deleted to appear as per attached.

Please delete col. 1-14 and substitute col. 1-14 as per attached.

Signed and Sealed this

Twenty-fifth Day of February, 1997

*Attest:*

BRUCE LEHMAN

*Attesting Officer*  *Commissioner of Patents and Trademarks*

United States Patent
Baratta

Patent Number: 5,528,942
Date of Patent: Jun. 25, 1996

[54] APPARATUS FOR MAXIMIZING CRITICAL BUCKLING LOADS FOR COMPRESSION TESTING

[76] Inventor: Francis I. Baratta, 138 Ridge St., Arlington, Mass. 02174-1737

[21] Appl. No.: 490,054

[22] Filed: Jun. 13, 1995

[51] Int. Cl.⁶ ............................................. G01N 3/02
[52] U.S. Cl. ............................................. 73/856; 73/818
[58] Field of Search ............. 73/818, 825, 855, 856, 73/857, 858, 859, 860

[56] References Cited

U.S. PATENT DOCUMENTS

| | | | |
|---|---|---|---|
| 3,559,473 | 2/1971 | Dudderar et al. | 73/818 |
| 4,393,716 | 7/1983 | Clark et al. | 73/818 |
| 4,686,860 | 9/1987 | Liu | 73/856 |
| 4,840,070 | 6/1989 | Ralfs et al. | 73/818 |
| 4,850,231 | 7/1991 | Ralfs et al. | 73/859 |
| 5,297,441 | 3/1994 | Smith et al. | 73/818 |
| 5,373,744 | 12/1994 | Parsons et al. | 73/818 |
| 5,388,464 | 2/1995 | Maddison | 73/856 |
| 5,431,062 | 7/1995 | Baratta | 73/856 |
| 5,435,187 | 7/1995 | Ewy et al. | 73/856 |

OTHER PUBLICATIONS

S. Timoshenko, *Strength of Materials*, Part I, 3rd. Ed., D. Van Nostrand Co., N.Y. 1958.

*Primary Examiner*—Richard Chilcot
*Assistant Examiner*—Max Noori

[57] ABSTRACT

Attempts to determine compression properties of materials from specimens having thin cross-sections or large slenderness ratios are thwarted because failure will first occur due to Euler buckling. The same problem exists when testing thin columns of various cross-sections and thin-walled cylinders as structural components, or in situ specimens cut out of thin structural components. The specimen can be: a dumbbell type, rectangularly-shaped, square-shaped, a thin coupon, a thin hollow cylinder, or specimens cut out of structural components. A simple way to increase the critical buckling force is presented while compressing laboratory specimens, specimens taken from structural components, or structural components having large slenderness ratios. The true compressive load is fully developed within the test piece such that the compression properties of the material can be determined without buckling. This can be accomplished at cryogenic, ambient, or elevated temperatures. A hollow cylinder, termed a buckling preventer, is utilized which is fitted and fixed to the ends of the sample by various attachments. These assemblies in turn are clamped at each end by commercially available hydraulicly-operated grips within the load train. The combined cross-sections of the hollow cylinder and the specimen act in concert to markedly increase the moment of inertia of the system. Since the Euler column buckling load is directly dependent upon the moment of inertia, a marked increase in this section properly will result in a correspondingly marked increase in the critical buckling load.

24 Claims, 7 Drawing Sheets

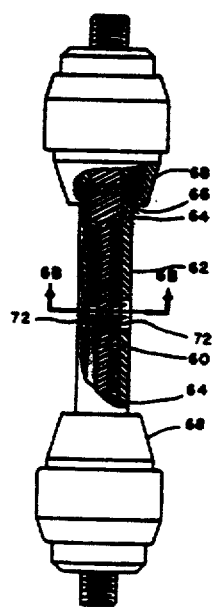

APPARATUS FOR MAXIMIZING CRITICAL BUCKLING LOADS FOR COMPRESSION TESTING

FIELD OF INVENTION

This invention solves the problem of and need for a simple method of increasing the critical buckling force during compression testing of laboratory specimens, columns of various cross-sections such as circular, rectangular and square etc.; and including thin-walled cylindrical structures, where all of these have large length-to-cross-sectional-thicknesses called, slenderness ratios, while allowing the applied compressive force to fully develop within the specimen or structure and thus determine valid mechanical compression properties of test materials.

BACKGROUND OF INVENTION AND PRIOR ART

When attempting to determine mechanical properties of homogeneous and composite materials while testing in compression samples taken from components whose slenderness ratio is large, such as thin sheets, columns, or thin-walled tubes, difficulties arise because the Euler column buckling load (see OTHER PUBLICATIONS) will be less than that required to fully test the specimen. Whether the test piece be a metallic, a ceramic, a polymer or a composite material this problem is ever present. Also in the field of mechanics of materials research, thin hollow cylinders are utilized as test specimens to determine the validity of failure hypotheses. Such hypotheses often require multi-axial loading which includes compression stressing. Again, the researcher faces the problem that the thin hollow cylindrical specimen may fail due to Euler buckling, depending upon its slenderness ratio, prior to attaining the desired data.

To demonstrate how Euler column buckling can interfere with the determination of mechanical properties consider the following realistic example:

Assume for the sake of demonstration that the exact compression strength or yield stress (or proportional limit) of a thin-walled steel component is desired after fabrication, and it is known that prior to the manufacturing process the compression yield strength is approximately 100 ksi. A test coupon is removed from the structure to determine its compression properties; it has an over all length L of 3 inches and rectangular cross-sectional dimensions of $b=1/2$ and $t=1/16$ inches. Since $P_y = S_y(A) = S_y(bt) = 100$ ksi $(1/2$ in $\times 1/16$ in$) = 3125$ lbs. $P_y$ is the expected load when testing in compression to determine the yield strength $S_y$ of the material and A is the cross-sectional area of the test specimen.

The critical Euler buckling load $P_{cr}$ for a column, or in this case a thin rectangular specimen with clamped end conditions having an axial length of L; and cross-sectional dimensions of length b and thickness t is given by the following general equation:

$$P_{cr} = 4 \pi^2 E\, I/L^2 \tag{1}$$

Where E, is the modulus of elasticity of the steel material, which is 30 million psi and I is the moment of inertia of the cross-section. In this case:

$$I = b\, t^3/12 \tag{1a}$$

Substitution of Eq. 1a into Eq. 1 gives:

$$P_{cr} = E\, \pi^2\, b\, t^3/3L^2 \tag{2}$$

Substitution of the above numerical values into Eq. 1 results in a critical buckling load $P_{cr}$ of 1339 pounds. It is seen from this example that buckling of the specimen will occur prior to obtaining the yield stress $S_y$ of the material and thus the determination of the desired mechanical properties will not be realized.

As seen from the above discussion, when manufacturing various structural components it is desirable to test such structures for mechanical strength. For example, in the airplane industry, some of the airplane parts are made of composite materials. It is desirable to test specimens of these parts for compression strength.

There are machines available to accomplish this type of testing. For example, during compression testing the specimen, such as a flat, thin, homogeneous sample (as already demonstrated) or a composite, sometimes referred to as a "coupon", is supported by a conventional test specimen holder (also referred to as a fixture) between the grips of the testing machine. The machine compresses the coupon along its lengthwise direction until it fails, whereupon the testing machine provides a read-out of the force provided to fail the specimen. Conventional type testing devices provide external support for coupons along their lengthwise axes which is required during compression testing to prevent Euler column buckling. However, test coupons should be supported in a manner so that buckling is eliminated without interfering with the transmission of the full load to each specimen. Also, if the coupon is a composite it should be supported in a manner so that the sublaminate buckling of the specimen, or any natural failure mode of interest is not restricted. In addition, during compression testing it is desirable to attach an extensometer or strain gages to the coupon to measure the amount of deformation or strain during compression.

These conventional fixtures have a large contact area with the test specimen which inherently transfers some of the test load to the fixture itself, resulting in an erroneous overestimate of the coupon's compressive strength. Also, an opening must be cut into the fixture to allow for open and filled hole compression tests. This makes it difficult to obtain valid strain measurements in the vicinity of the opening. Existing compression fixtures support faces of the test specimen. While these fixtures restrict the Euler column buckling, they also restrict the valid sublaminate buckling failure mode of composite samples. Specimen designs based on stable column sections have been used to measure compression properties of composites. However, these specimens have very restrictive application and are not suitable for general use.

A number of conventional support devices has been disclosed in U.S. Patents, see REFERENCES CITED. For example, U.S. Pat. No. 683,184 by Rockwell shows a clamp having four rectangularly arranged blocks connected together in pairs by compression and expansion screws. In addition, U.S. Pat. No. 2,350,060 by Montgomery and U.S. Pat. No. 2,368,900 by Templin disclose compression testing devices for thin specimens that include a pair of T-shaped jaws having small diameter rollers to engage the surfaces of the specimen. And U.S. Pat. No. 4,840,070 by Rolfs et al., utilizes a laminate compression tester which includes a pair of adjustable stabilizing jaws having end segments that engage specimen grips of the testing machine. Finally U.S. Pat. No. 5,297,441 by Smith et al., describes three embodiments: The first embodiment supports the test piece along both of its lengthwise edges while engaging between the grips of the testing machine, in the second the apparatus supports the test piece along only one of its edges, and in the third embodiment, the apparatus includes grip plates which are mounted to the test machine and engage a portion of the test specimen while the remainder of the specimen is supported along its lengthwise edges by stabilizer plates.

All of the above described inventions, to some degree, restrain the applied force such that the force is neither fully allowed to be developed in the test piece nor is it accurately known. This results in an erroneous measurement of this force leading to an error in the determination of the compression strength of the test sample.

SUMMARY OF INVENTION

Attempts to determine properties of materials when testing in compression from specimens having a thin cross-section or even specimens that have relatively large cross-sections and correspondingly large slenderness ratios are thwarted, because failure will occur due to Euler buckling prior to the realization of the objective. The same problem exists when testing columns of various cross-sections and thin-walled cylinders as structural components, depending upon their slenderness ratios, or in situ specimens cut out of thin structural components.

This invention presents an improved but simple method of precluding buckling while determining mechanical properties when testing in compression of laboratory test samples, columns and cylindrical structural components. The improvement is due to what has already been mentioned in U.S. Pat. No. 5,431,062 by Baratta, but termed here a buckling preventer. Briefly, the buckling preventer can be described as an assembly that surrounds the specimen with a hollow tube and fixes the ends of the specimen to the tube by mechanical means and forces the two components to behave as one through the use of various connections and/or the use of commercially available hydraulic grips. In this way, the moment of inertia of the combined structure is markedly increased over that of the test piece alone and the effect of the inherent bending moment is greatly reduced. Because one of the major parameters in the Euler column buckling equation, (refer to OTHER PUBLICATIONS; that by Timoshenko) is directly dependent upon the moment of inertia of the cross-section (see Eq. 1 above). Any increase in this cross-sectional property will markedly increase the critical buckling force, and in many testing situations eliminate buckling and allow the full mechanical property description of the test material.

The invention can accommodate a round dumbbell type specimen or one of a different cross-section, i.e., rectangular, square, or it can be a thin hollow cylinder. The test piece can be either pinned or threaded and/or bonded at its ends to the bending moment absorber; or the sample can be rectangularly-shaped or have a square-shaped cross-section, with semi-circular spacers having appropriate cut-outs to fit and accommodate the particular cross-sections, which are employed at each end and pinned or threaded and/or bonded between the specimen and the, buckling preventer, see U.S. Pat. No. 5,431,062. Also, if the modulus of elasticity of the buckling preventer is less than that of the specimen, while their failure strength ratio is greater than their modulus ratio, then failure will occur in the sample and the buckling preventer will be reusable.

The device can be readily adapted to commercially available ancillary testing equipment and instrumentation such that it can operate at cryogenic, room, midrange and at extremes of elevated temperatures and still allow the determination of compressive stress-strain data and failure strength of the test sample.

BRIEF DESCRIPTION OF THE DRAWINGS

FIG. 1 is a side view of a conventional testing machine and a conventional fixture for a test specimen;

FIG. 2 is an isometric view of the conventional specimen fixture shown in FIG. 1;

FIG. 3 is a plan view of a conventional test specimen;

FIG. 4A is a view of a circular cross-sectioned specimen;

FIG. 4B is a view of a thin hollow cylindrical cross-sectioned specimen;

FIG. 4C is a view of a thin rectangular cross-sectioned specimen;

FIG. 5A is a view of a specimen having a circular cross-section and the cross-section of the buckling preventer;

FIG. 5B is a cross-sectional view of a thin hollow specimen and the cross-section of the buckling preventer;

FIG. 5C is a view of a specimen having a thin, rectangular cross-section and the cross-section of the buckling preventer;

FIG. 6A is a cross-sectional view of a round dumbbell specimen shown inserted and pinned within the buckling preventer and this assembly, in turn, is grasped at both ends by hydraulically-operated collet grips;

FIG. 6B is a cross-sectional view of FIG. 6A, shown for clarity;

FIG. 7A is a cross-sectional view of a thin hollow cylindrical specimen with filler spacers shown inserted and pinned within the buckling preventer and this assembly, in turn, is grasped at both ends by hydraulically-operated collet grips;

FIG. 7B is a cross-sectional view of FIG. 7B, shown for clarity;

FIG. 8A is a cross-sectional view of a thin, rectangular specimen (a coupon) shown inserted and pinned with spacers within the buckling preventer and this assembly, in turn, is grasped at both ends by hydraulically-operated collet grips;

FIG. 8B is a cross-sectional view of FIG. 8A, shown for clarity;

FIG. 9A is a cross-sectional view of of a round dumbbell specimen inserted and pinned within the buckling preventer;

FIG. 9B is a cross-sectional view of FIG. 9A, shown for clarity;

FIG. 10A is a cross-sectional view of a dumbbell specimen shown inserted and shrunk-fitted (or fixed by other means; not shown) within a buckling preventer in the form of a strut assembly;

FIG. 10B is a cross-sectional view of FIG. 10A, shown for clarity.

PREFERRED EMBODIMENT

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

The following paragraphs describe the preferred embodiments, where the figures are discussed in detail to aid in explaining the operating proposed principle. First however, a section entitled Conventional Test Fixtures is presented, followed by a section called Critical Buckling Load. These two sections are presented to better demonstrate the operating principle of the present invention as applied to test specimens which can be considered columns having various cross-sections and then comparing the increase in the critical buckling loads when these configurations are tested in the proposed invention.

Conventional Test Fixtures

As mentioned above, before describing the present invention in greater detail, a brief description of a conventional test fixture and testing machine will be provided which represent those in current use. Referring first to FIG. 1 there is shown a portion of a conventional compression/tension testing machine indicated at 20. In the Figure, the testing machine 20 includes a model 647 hydraulic wedge grip which is part of a MTS 810 test system manufactured by MTS Corporation of Minneapolis, Minn. The testing machine 20 includes an upper wedge 22 having a pair of jaws (also referred to as "grips") 24 and a lower wedge 26 having a pair of grips 28. The grips 24,28 are movable between a closed position (shown in FIG. 1) where the grips engage a conventional specimen fixture indicated at 30 and an open position (not shown) where the grips are spaced apart from the fixture 30.

As shown in FIGS. 1 and 2, the specimen fixture 30 includes an upper large grip portion formed by identical left, right plates 32,34 respectively, and a separate smaller, lower grip portion formed by identical left, right plates 36,38, respectively. A specimen 40 (FIG. 3) having a rectangular plan configuration and a rectangular cross-section is inserted between the left and right grip plates of the upper and lower grip portions and the opposing plates are then bolted together through openings 42 by bolts (not shown). The grip plates are bolted together to extend entirely across both faces of the specimen 40 and in a manner such that the upper and lower plates are vertically spaced apart from each other slightly by gap 44. A hole 45 is made in one of the plates to allow for open and filled hole compression tests. Briefly, an open hole test involves a rectangular specimen having a circular center hole. The purpose of this test is to determine the influence of properties caused by a hole in the material. On the other hand, a filled hole test uses the same specimen as the open hole test except a fastener is installed in the hole prior to the test. This makes it difficult to obtain measurements of strain, etc. in the vicinity of the hole 45 because if the hole is made large enough to contain the necessary instrumentation to measure strain, there is a high probability of a local buckling failure caused by loss of cross-sectional properties, or specifically the loss of the moment of inertia due to the opening.

With the presence of the gap 44, a slight movement together of the upper and lower portions of the testing machine is permitted in order to determine the compression strength of the specimen 40 and to avoid gross reaction of the compression load through the fixture 30. In order to support the specimen 40 across the gap 44 and to prevent unwanted buckling of the specimen at the gaps, a lower blocking plate 46 is attached to the outer surface of the right grip plate 38 across gap 44, and an upper blocking plate 48 is bolted to the outer surface of the upper left grip plate 32 across another gap 44. Even though the gross reaction of the compressive buckling load is minimized by the gap 44 and blocking plates 46,48 and the sandwiching left and right plates 32,34 (see FIG. 1 and FIG. 2), there remains a reduction due of the load transfer to friction from the testing machine to the sandwiched specimen 40 causing inaccurate mechanical property determination.

The principle that allows the increase in the critical buckling load in the mechanical property determination when testing in compression using the present invention is mathematically demonstrated in the following:

Critical Buckling Load

In order to show the operating principle of the proposed invention, the buckling loads for different columns having three cross-sectional shapes are determined: a solid circular cross-section 60, a thin hollow cylinder 110 and a rectangular cross-section 80; each of these shapes are shown in FIGS. 4A, 4B, and 4C, respectively. These columns, or specimens, are then presumed to be tested in the proposed device, such as that shown in FIGS. 6A and 6B; 7A and 7B; and 8A and 8B where the addition of the buckling preventer 62, shown in the cross-sections given in FIGS. 4A, 4B, and 4C, demonstrates the improvement for each case.

The critical buckling load for a column with fixed ends is given by Eq. 1 above. Note that one of the important parameters is the moment of inertia of the cross-section. The moment of inertia of the cross-sections shown in FIGS. 4A, 4B, and 4C, which will be called Case 1, Case 2 and Case 3, respectively are:

$$I_1 = \pi R^4/4, \qquad (3)$$

$$I_2 = \pi[R_o^4 - R_i^4]/4, \text{ and} \qquad (4)$$

$$I_3 = b\, t^3/12 \qquad (5)$$

Where R is the radius of the circular cross-sectioned specimen (FIG. 4A), $R_o$ is the outer radius and $R_i$ is the inner radius of the thin hollow cylinder (FIG. 4B) and b and t are the length and thickness of the rectangular cross-section (FIG. 4C).

Consider now encompassing each of these specimens with a hollow cylinder, the buckling preventer, and being of the same material as the specimens. The ends of each specimen are fixed to the buckling preventer 62 and each end clamped by commercially available hydraulically-operated grips 68, as shown for example in FIGS. 6A and 6B; 7A and 7B; and 8A and 8B. Now the moment of inertia of each of these combined cross-sections, shown in FIGS. 5A, 5B, and 5C, associated with Cases 1, 2, and 3, respectively are:

$$I_1 = \pi[R^4 + (R_3^4 - R_2^4)]/4, \qquad (6)$$

$$I_2 = \pi[(R_o^4 - R_i^4) + (R_3^4 - R_2^4)]/4, \qquad (7)$$

and:

$$I_3 = bt^3/12 + \pi(R_3^4 - R_2^4)/4 \qquad (8)$$

Where $R_3$ and $R_2$ are the inner and outer radius of the buckling preventer, respectively, as shown in FIG. 5A; and indicated in FIGS. 5B, and 5C.

Because the remaining parameters in Eq. 1, i.e., $\pi$, E, and L, the general formula for the critical buckling load, are the same for both the single cross-sections and the combined cross-sections, a comparison of buckling loads can be effected by simply dividing each of the above equations by the equation representing the respective moment of inertia of the single cross-section, e.g., divide Eq. 6 by Eq. 3, etc. These operations result in the following equations that define the critical buckling ratios $R_{cr1}$, $R_{cr2}$, and $R_{cr3}$:

$$R_{cr1} = 1 + (R_3/R)^4 - (R_2/R)^4, \qquad (9)$$

$$R_{cr2} = 1 + (R_3^4 - R_2^4)/(R_o^4 - R_i^4) \qquad (10)$$

$$R_{cr3} = 1 + 3\pi(R_3^4 - R_2^4)/bt \qquad (11)$$

The above formulas mathematically indicate the idealized improvement in the critical buckling load when utilizing the proposed invention; for example consider each of the three cases by assigning practical numbers to the various parameters. Therefore, let: $R = 1/4$ in., $R_i = 0.40$ in., $R_o = 0.50$ in., $b = 1/2$ in., $t = 1/16$ in., $R_3 = 0.70$, $R_2 = 0.60$ in.

Calculations for the critical buckling ratio according to Eqs. 9, 10, and 11 are summarized in the following table: Table 1

| case: | Critical Buckling Ratio |
|---|---|
| 1 | 29.3 |
| 2 | 3.4 |
| 3 | 8,532 |

The above table demonstrates the gain in the critical buckling force by using the presented invention as a function of the type of test specimen shown in FIGS. 4A, 4B, and 4C. It is noted that the critical buckling load was 1339 pounds as obtained for the rectangularly cross-sectioned specimen from Eq. 1, for the example previously cited, case 3. But, if the present device had been employed the increase in force to cause buckling, as indicated in the above table, would have been 8,532 times greater than 1339 pounds. This is an idealized result because the fixity at the ends of the specimen will not be completely rigid. Nevertheless, the gain in the critical buckling load will be considerably greater than 1339 pounds and certainly greater than than the yield load of 3125 pounds, and thus the determination of the desired mechanical property evaluation could have been readily realized.

So as to be able to obtain the compression properties of the specimen material, the load distribution from the testing machine to the buckling preventer and the specimen needs to be known; consider the following analysis:

Referring to FIG. 9A and FIG. 9B, it is assumed that the buckling preventer and the specimen are of different materials each having a modulus of elasticity of $E_a$ and $E_s$, respectively. Also the connections, such as the pins 66, at the buckling preventer interfaces with the specimen are considered to be rigid, i.e., the assembly acts as one solid body. This is not completely correct in that there will be some flexibility at the interfaces, but this can only be determined by experimentation. Nevertheless, it shall be assumed that the ideal case exists so as to simplify the mathematics and easily demonstrate the operating principle.

In FIG. 9A, the axial displacement $d_s$ of the specimen 60 and the displacement $d_a$ of the buckling preventer 62 during testing (where both having a fixed length of L) are: $d_s = L \epsilon_s$ and $d_a = L \epsilon_a$, respectively, but $d_s = d_a$, and $L(S_s/E_s) = L(S_a/E_a)$. Where $S_s$ and $S_a$ are the axial stresses in the specimen and the buckling preventer, respectively; also $\epsilon_s$ and $\epsilon_a$ are the axial strains in the specimen and the buckling preventer, respectively. Note that for simplicity the diameter of the heads of the specimen are assumed to be the same diameter as its gage section. Therefore:

$$S_s/E_s = S_a/E_a, \text{ or } S_a = S_s(E_a/E_s) \qquad (12)$$

Also the total load $P_t$ to the specimen and the buckling preventer is:

$$P_t = S_s A_s + S_a A_a \qquad (13)$$

And utilizing Eq. 13, we obtain:

$$P_t = S_s[A_s + A_a(E_a/E_s)], \text{ and } P_a = P_t - S_s A_s \qquad (14)$$

Also:

$$S_s = P_t/[A_s + A_a(E_a/E_s)] \qquad (15)$$

And from Eq. 13 we obtain:

$$S_a = (P_t - S_s A_s)/A_a \qquad (16)$$

Equations 13 and 14 will allow an estimate of the idealized load distribution between the buckling preventer and the specimen. Equations 15 and 16 will allow an estimate of the stress in the specimen and the buckling preventer, respectively. However, a more exact method using experimental techniques is subsequently suggested so as to accurately determine the mechanical properties of the specimen material.

Now turning to the present invention, which pertains to an apparatus for compression testing an elongate workpiece, a specimen in the form of a dumbbell shape, shown in FIGS. 6A and 6B. The apparatus includes a hollow cylinder, termed a buckling preventer 62, which encompasses the workpiece, or test specimen 60. The buckling preventer is closely fitted and pinned 66 or can be threaded and/or bonded to the ends of a dumbbell specimen. Rectangularly-shaped or square-shaped cross-sectioned specimens can also be tested by utilizing appropriate spacers at their ends which are then pinned or threaded and/or bonded to the buckling preventer; this will be discussed later. These assemblies, in turn, are clamped at their ends by commercially available hydraulically-operated grips 68, shown in FIG. 6A and 6B, within the load train, thus forcing the specimen to act as an integral part of the buckling preventer 62. The moment of inertia of the combined cross-sections of the assembly, including the specimen, is markedly increased. The buckling preventer has a very large cross-sectional moment of inertia compared to that of the specimen (if it were to act alone). This markedly increases the moment of inertia of the assembly and thereby increases the critical force at which buckling will occur; at the same time, the axial compression force is allowed to be distributed from the testing machine to the specimen without restraint.

When testing in the linear mode regime, i.e., linear response of the material, the material for the buckling preventer can be chosen to be dissimilar to that of the specimen such that the modulus of the elasticity ratio of the buckling preventer to that of the specimen is less than 1.0; while their yield strength ratio is greater than their modulus ratio. Because the buckling preventer and the specimen are fixed to each other, the load distribution during testing can be determined. With the aid of appropriate instrumentation and prior knowledge of the modulus ratio, the stress applied to the specimen will be known, as well as stress-strain data during testing. Failure will occur in the test specimen before the buckling preventer reaches its yield or failure stress and thus be reusable.

A similar approach can be adopted for testing in a nonlinear mode, i.e., testing in the extremes of elevated temperatures, by heating only the specimen and cooling the encompassing buckling preventer. Again, if the buckling preventer and specimen are initially of dissimilar materials and their modulus of elasticity ratio is less than 1.0; with the use of appropriate instrumentation the stress-strain curve of the specimen material will be known, as well as its compressive properties. As before, the buckling preventer will be available for reuse.

Alternatively, the buckling preventer can be fabricated from the same material as the specimen and this assembly heated for testing in the nonlinear mode of operation. With appropriate instrumentation the desired compressive properties of the test material will be known.

It is noted that most engineering materials when heated, and when being tested within the elastic regime will, nevertheless, exhibit a lesser modulus of elasticity than that obtained at ambient conditions, and therefore will be less stiff so that specimens of large slenderness ratios will have greater tendency to buckle. The use of the proposed invention in such a condition allows the buckling preventer to provide an increase in the moment of inertia and thus will reduce the possibility of critical buckling.

Again referring to FIG. 6A and FIG. 6B, the axial strain can be monitored via electric-resistance strain gages 88 bonded to the buckling preventer 62, or for elevated temperature operation, the axial displacement of the buckling preventer can be obtained using laser type extensometers (not shown). An additional extensometer can simultaneously be aimed through the ports 72 at the specimen gage diameter during elevated temperature operation. This allows the knowledge of the displacement or strain in the specimen 60 due to compressive loading and various temperature environments, and thus the stress as a function of temperature and the strength of the material can be determined. Further mathematical details of testing in the linear and nonlinear tensile mode of operation are given in U.S. Pat. No. 5,431,062 by Baratta; they are applicable to the compressive mode of testing as well, and thus are not repeated here.

To insure intimate contact during cryogenic temperature testing, the buckling preventer material can be chosen such that its linear coefficient of thermal expansion is greater than that of the specimen material. At elevated temperatures the chosen thermal expansion ratio should be reversed. Ambient temperature testing will require a slip-fit between the buckling preventer and the specimen. The specimen material, the temperature at which testing is to be accomplished, and the ratio of the modulus of elasticity of the buckling preventer to the specimen material will dictate the material to be used for the buckling preventer. Further discussion of such details are not necessary to the understanding of the presented concept.

The test fixtures shown in FIGS. 6A, 7A and 8A can be used for both static and dynamic loading at various temperature environments. However, even though dynamic loading with its required ancillary equipment and instrumentation can be an adjunct to the static fixtures, is not further discussed because it is not necessary to the understanding of the principle of the invention. Therefore, only static loading at various temperature environments have been considered and discussed. Nevertheless, such discussions are germane to the dynamic loading regime, as well.

Turning now to the first embodiment and returning to FIGS. 6A, and 6B, a dumbbell specimen 60 is shown inserted and pinned 66 at each of its head-ends 64 within a tube, called a buckling preventer, 62; this tubular sleeve also has ports 72 that allow deflection observations of the specimen and strain gages 88 that allow strain determination. The buckling preventer and the specimen are fitted snugly or even slightly shrink-fitted within each other to insure intimate contact at their interfaces. The assembly in turn is grasped by commercially available hydraulic grips 68. The dumbbell specimen 60, with accompanying holes for pins 66, or threaded holes for bolts or screws, can be designed within the present state-of-the art and the pin, bolt or screw material chosen, such that failure will be insured within the central gage section of the specimen design. It is noted that only the pins are shown for demonstrative purposes.

In the above described embodiment the buckling preventer 62 is a tube which has drilled holes at the top and bottom and a prepared sample or specimen 60 with matching top and bottom holes is encompassed by the buckling preventer. Each hole in the buckling preventer is connected by a pin, bolt or screw (these not shown) to a matching hole in the sample. These fasteners may terminate within the sample or may be drilled through the sample and engage holes on both sides of the tube. At least one through-pin, bolt or screw or two terminating pins, bolts or screws aligned oppositely on the sample will be used at each end of the sample.

There are a number of various fastening methods other than those given above that are subsequently described, but for the sake of clarity are not presented in the figures.

The important first embodiment shown in FIG. 6A is the buckling preventer 62 connected to the specimen 60 and the assembly rigidly clamped together by the hydraulically-operated grips 68 while being loaded in compression. As previously mentioned, the buckling preventer acts to increase the moment of inertia from only that of the specimen, if it were being tested alone, to that of the complete assembly, thus markedly increasing the critical buckling load.

Returning to FIG. 6A and FIG. 6B, ports 72 are provided in the buckling preventer 62 to allow observation of the specimen 60 during testing for extensometer measurements or to provide openings for the lead wires attached to the strain gages (not shown). Strain gages 88, as shown in FIG. 6B, can also be bonded to the outside of the buckling preventer. In this way the distribution of the known load from the mechanical testing machine to both the specimen 60 and the buckling preventer 62 will also be known, if the modulus of elasticity of each material has been determined previously. Alternatively, if only one of the members is strain-gaged the force transmitted to the other member can be deduced since the total force is known from the testing machine. In addition, the stress-strain curve of the test specimen material within the elastic region can also be obtained which will allow the determination of the compressive strength of the material.

FIGS. 7A and 7B show a thin hollow specimen 110 with closely fitted cylindrical filler spacers 112 and 114 located at each end of the sample (but shown only at one end for convenience). These components are encompassed by the closely fitted buckling preventer 62 with ports 72, which in turn are pinned 66 together. The assembly is gripped at its ends by commercially available hydraulically-operated grips 68. Although the strain gages are not shown so as to simplify the drawings, they can be bonded to the specimen/and or the buckling preventer for displacement determination. The buckling preventer, the spacers and the pins can be fitted snugly to each other or even slightly shrink-fitted within each other to insure intimate contact at their interfaces. It is noted that only the pins are shown for demonstrative purposes and for the sake of clarity only these connectors are shown in the figures. However, there are many fastener methods that can be employed and these are subsequently discussed.

A rectangular cross-sectioned coupon, shown in FIGS. 8A and 8B, or a square cross-sectioned specimen (not shown), that can be stressed in a compressive mode, can also be tested in an arrangement similar to that shown in FIG. 6A and FIG. 6B. FIGS. 8A and 8B show the complete assembly, where the coupon 80, is sandwiched at its ends by semi-cylindrical spacers 90 and pinned 66 or joined in the same ways described above at both ends (only one end is shown cross-sectioned) to the encompassing buckling preventer 62; this in turn is grasped at its ends by a set of hydraulically-operated grips 68. Again, strain gages on the buckling preventer (not shown), or an extensometer can be used to obtain the strain in the buckling preventer 62. The displacement of the coupon (or square cross-sectioned specimen) can be obtained by strain gages 118, or observed with an extensometer through the ports 72 of the buckling preventer provided for that purpose.

A second embodiment where the prepared sample is slip-fitted into the buckling preventer and these two components are clamped together at the top and bottom ends by mechanically activated devices, such as two drillpress chucks, or two mechanically operated collet grips; this assembly in turn is further clamped together by two hydraulically-operated grips attached to the ends of the testing machine. Alternatively, a set of hydraulically-operated grips can be used in place of the mechanically operated devices. Also, shrink-fitted or threaded joints, or encapsulation of the specimen ends within the inside diameter of the buckling preventer with a low temperature melting, metallic material, and/or bonding, such as adhesive bonding, brazing or welding, can replace the pinned joints at the specimen head-ends, or a combination thereof can be employed.

In a third embodiment the buckling preventer can be fabricated from any appropriate structural material including a polymer, cast as a hollow cylinder around the specimen or where the prepared sample is placed within a mold and a material with a very low modulus of elasticity compared to that of the specimen, such as a catalyzed elastomer for example, molded as a tube around the sample, providing grip surfaces at the top and bottom that are molded to the sample. (Note that if the modulus of elasticity of the buckling preventer is very much less than that of the the specimen, then the axial stress in the buckling preventer approaches zero; see Eq. 12 above). Knurled or serrated surfaces in the grip area may be used to enhance the adhesion between the elastomeric material and the sample, as long as the surface modifications have no effect on the sample or the subsequent test results.

In a fourth embodiment the surrounding tube, the buckling preventer, can be a metallic, a ceramic, or a polymeric material, or even a composite tubular sleeve; all having an interference fit with the prepared sample. The tube is heated to an elevated temperature in an oven or any other appropriate device, such as a hot plate, then slipped over the prepared specimen which is chilled. The tube is then cooled causing a tight interference fit at the ends of the prepared sample, which can be fitted into a testing machine.

In a fifth embodiment, a high temperature steel, such as a superalloy steel, or a ceramic material can be utilized as a buckling preventer, with an interference fit joining the top of the prepared sample to the top end of the buckling preventer and the bottom end of the prepared sample to the bottom end of the buckling preventer, allowing its use at high testing temperatures.

In a sixth embodiment the buckling preventer material can be chosen to have an appropriate linear coefficient of thermal expansion compared to the test sample such that the buckling preventer radially compresses the sample at its top and bottom ends when testing at both cryogenic and elevated temperatures.

In a seventh embodiment the buckling preventer material can be chosen such that its modulus of elasticity is less than that of the prepared sample specimen. In this way the specimen during testing supports a major portion of the applied force and will fail leaving the buckling preventer intact for reuse.

An eighth embodiment allows the buckling preventer system to be used not only for applying either static or dynamic forces in compression, but to apply torque, tension or a combination of these forces, as well as fatigue, if desired.

A ninth embodiment is shown in FIG. 10A and FIG. 10B, where a plurality of strut elements 122 joined by any of the present state-of-the-art joining methods that will bond in a rigid manner, such as welding 124 to hoops 120 fitted and fixed, by means previously described, to the head-ends 64 of the specimen can also be employed. The marked increase in the moment of inertia provided by the buckling preventer in the form of strut assembly, 120 and 122 acting in concert with the specimen 60 provides a respondingly large increase in the critical buckling force during compression testing.

I claim:

1. A method to determine the compression properties of a material where a sample of said material is prepared for testing, said sample having a top end and a bottom end, said top and said bottom ends providing grip surfaces for a testing machine and said sample is firstly enclosed within surrounding means which has an upper end and a lower end; said surrounding means are secondarily closely fitted to said sample top end and said sample bottom end, and where, thirdly, the sample is clamped where said top end of said sample is affixed by affixing means to the upper end of said surrounding means, and where said bottom end of said sample is affixed by affixing means to said lower end of said surrounding means, and where said sample and surrounding means are finally clamped by clamping means within a testing device and when, the test device is then activated, the surrounding means, acts as a buckling preventer, which increases the moment of inertia of said sample precluding the possibility of critical buckling.

2. The claim in 1 where said sample is a test specimen having a dumbbell shaped cross-section, or a thin hollow cylindrical cross-section, or is a thin rectangularly-shaped cross-sectioned coupon removed from a structural component.

3. The claim in 2 where said surrounding means is a tube.

4. The claim in 2 where said surrounding means is a plurality of strut members affixed to hollow cylinder ends.

5. The claim in 2 where said affixing means is a pin or bolt.

6. The claim in 2 where said affixing means is an adhesive joint.

7. The claim in 2 where said affixing means is a shrink fit between the surrounding means and the top end of the sample and the surrounding means and the bottom end of the sample.

8. The claim in 2 where said affixing means is a threaded joint.

9. The claim in 2 where said affixing means is a soldered joint.

10. The claim in 2 where said affixing means is a brazed joint.

11. The claim in 2 where said affixing means is encapsulation within a cast or poured elastomer.

12. The claim in 2 where said affixing means is encapsulation of the specimen ends within the surrounding means with a metallic material having a low melting temperature.

13. The claim in 2 where said clamping means are mechanically activated joints, such as two drillpress chuck mechanisms or two collet grips or two hydraulically-operated grips located at each end of the surrounding means, which is a buckling preventer.

14. The claim in 2 where said clamping means are two hydraulically-operated jaws located at each end of the surrounding means, called a buckling preventer.

15. The claim in 2 where said surrounding buckling preventer tube is a super alloy steel or a ceramic tube, thus allowing a functional buckling preventer method for high temperature tests of metals and ceramics.

16. The claim in 2 where said surrounding buckling preventer tube material is chosen to have a linear coefficient of thermal expansion less than that of the prepared sample, such that a radial compression is provided at the top and bottom ends of the test sample when testing at elevated temperatures.

17. The claim in 2 where said surrounding buckling preventer tube material is chosen to have a linear coefficient of thermal expansion greater than that of the prepared sample, such that a radial compression is provided at the top and bottom ends of the test sample when testing at cryogenic temperatures.

18. The claim in 2 where said surrounding buckling preventer material is chosen to have a lower modulus of elasticity than that of the prepared sample, such that the sample will support a greater portion of the applied load and thus fail; leaving the buckling preventer intact and allowing it to be reusable.

19. The claim in 2 where said surrounding buckling preventer is used for static testing.

20. The claim in 2 where said surrounding buckling preventer is used for dynamic testing.

21. The claim in 2 where said surrounding buckling preventer is used for cyclic fatigue testing.

22. A device to test specimens that are columnar in form where a prepared sample, which has a top end and a bottom end enclosed within a surrounding sleeve which is a buckling preventer which has a top end and bottom end, where said prepared sample is affixed at said top end to said top end of said surrounding sleeve and where said prepared sample is affixed at its said bottom end to said bottom end of said surrounding sleeve and where said top end of said surrounding sleeve is gripped by the top jaw of a testing machine and where said bottom end of said surrounding sleeve is gripped by the bottom end of the bottom jaw of a testing machine, and where said surrounding sleeve, which is a buckling preventer, acts to align said top and bottom ends of said sample within said testing machine; preventing premature failure by buckling of said test sample.

23. A method to test specimens that are columnar in form where a prepared test sample is enclosed within a closely conforming tubular sleeve or buckling preventer to contain it, and affixed to said tubular sleeve at each end, and where the ends of said tubular sleeve and said contained sample are gripped within a testing machine, where said tubular sleeve provides additional moment of inertia to the said prepared test sample it contains and reduces possibility of buckling.

* * * * *